(12) United States Patent
Perlman

(10) Patent No.: US 9,561,079 B2
(45) Date of Patent: Feb. 7, 2017

(54) NO-CONTACT COVER FOR STETHOSCOPES AND OTHER DEVICES

(71) Applicant: Alan Scott Perlman, Bergenfield, NJ (US)

(72) Inventor: Alan Scott Perlman, Bergenfield, NJ (US)

(*) Notice: Subject to any disclaimer, the term of this patent is extended or adjusted under 35 U.S.C. 154(b) by 0 days.

(21) Appl. No.: 14/940,319

(22) Filed: Nov. 13, 2015

(65) Prior Publication Data

US 2016/0066996 A1    Mar. 10, 2016

Related U.S. Application Data

(63) Continuation of application No. 14/709,569, filed on May 12, 2015, now Pat. No. 9,220,565.

(60) Provisional application No. 61/993,854, filed on May 15, 2014.

(51) Int. Cl.
| | | |
|---|---|---|
| *A61B 7/02* | (2006.01) | |
| *A61B 19/02* | (2006.01) | |
| *A61B 7/00* | (2006.01) | |
| *B65D 85/00* | (2006.01) | |

(52) U.S. Cl.
CPC ............ *A61B 19/026* (2013.01); *A61B 7/00* (2013.01); *A61B 7/02* (2013.01); *A61B 46/10* (2016.02); *A61B 50/30* (2016.02); *B65D 85/54* (2013.01); *A61B 2050/314* (2016.02); *A61B 2562/247* (2013.01); *Y10T 428/1334* (2015.01)

(58) Field of Classification Search
CPC ........................................................ A61B 7/02
USPC ........................................................ 181/131
See application file for complete search history.

(56) References Cited

U.S. PATENT DOCUMENTS

| | | | | |
|---|---|---|---|---|
| 5,269,314 A | * | 12/1993 | Kendall | A61B 7/02 181/131 |
| D344,798 S | * | 3/1994 | Baskin | A61B 7/02 D24/134 |
| 5,428,193 A | * | 6/1995 | Mandiberg | A61B 7/02 181/131 |
| 5,448,025 A | * | 9/1995 | Stark | A61B 7/02 181/131 |
| 5,539,162 A | * | 7/1996 | Tuttle | A61B 7/02 181/131 |
| 5,623,131 A | * | 4/1997 | Earnest | A61B 7/02 128/DIG. 15 |
| 5,686,706 A | * | 11/1997 | Wurzburger | A61B 7/026 181/131 |
| 5,921,941 A | * | 7/1999 | Longobardo | A61B 7/02 600/528 |
| 6,186,957 B1 | * | 2/2001 | Milam | A61B 7/02 600/528 |
| D505,491 S | * | 5/2005 | Nessel | A61B 7/02 D24/134 |
| 7,823,690 B2 | * | 11/2010 | Hirsch | A61B 7/02 181/131 |
| 7,832,021 B2 | * | 11/2010 | Singer | A41D 19/0082 2/160 |
| 8,051,946 B1 | * | 11/2011 | Murad | A61B 7/02 181/131 |
| 9,220,565 B2 | * | 12/2015 | Perlman | A61B 19/026 |

(Continued)

*Primary Examiner* — Forrest M Phillips
(74) *Attorney, Agent, or Firm* — Ronald D. Slusky

(57) ABSTRACT

Disposable covers for articles including stethoscopes are configured in such a way as to reduce the likelihood of the transmission of microbes among the patient; the stethoscope, medical device or other article; and the user/careprovider.

24 Claims, 16 Drawing Sheets

(56) References Cited

U.S. PATENT DOCUMENTS

| | | | | |
|---|---|---|---|---|
| 2002/0170771 | A1* | 11/2002 | Milam | A61B 7/02 181/131 |
| 2005/0257996 | A1* | 11/2005 | Brown | A61B 7/02 181/131 |
| 2005/0257997 | A1* | 11/2005 | Vick | A61B 7/02 181/131 |
| 2007/0074929 | A1* | 4/2007 | Garcia | A61B 7/02 181/131 |
| 2013/0341223 | A1* | 12/2013 | Fong | A61B 7/02 206/363 |

* cited by examiner

10

10

PATIENT CONTACT SURFACE

110

110

NO-CONTACT COVER FOR STETHOSCOPES AND OTHER DEVICES

CROSS-REFERENCE TO RELATED APPLICATIONS

This is a continuation of U.S. patent application Ser. No. 14/709,569, filed May 12, 2015, which claimed the benefit of provisional application Ser. No. 61/993,854 filed May 15, 2014, the disclosure of which is hereby incorporated by reference as though fully set forth herein.

BACKGROUND

The transmission of micro-organisms between patients in health care settings remains a major health problem and accounts for significant morbidity and mortality. Based upon considerable evidence, it is accepted that contaminated hands of health care workers are a major route of cross-infection amongst patients. Despite this recognized risk for transmission and the subsequent incorporation by medical facilities of hand hygiene practices, the rate of transmission of hospital-acquired organisms has not declined appreciably in recent years. There is increasing evidence that stethoscopes are a major vector for the patient-patient transmission of infectious organisms.

One strategy for addressing potential bacterial contamination of the stethoscope head is the one-use disposable stethoscope. This approach, while somewhat effective, is expensive. Disposable stethoscopes are also of inferior acoustic quality than standard stethoscopes.

Another strategy is to disinfect the stethoscope head using alcohol pads or hand cleanser. However, although several studies have indicated that although this is an effective means of reducing bacterial colony counts on the diaphragm and bell of stethoscopes, a 2007 review of the subject revealed that 45-68% of physicians and nurses surveyed reported "never" or "rarely" cleaning their stethoscopes. Another survey reported that only 24% of respondents disinfected their stethoscopes after every use.

SUMMARY

An additional strategy known in the art is a disposable cover or barrier that prevents contact between the stethoscope head and the patient. The most common approaches are a cap-like cover for either the diaphragm or the bell portions of the head of a stethoscope or a full-length stethoscope sleeve, such as those marketed under brand names Stethocap and Stethosleeve, respectively.

The present inventor has observed that the cap-like cover as known in the art is advantageous in that it fits snugly on diaphragm or bell, can be conveniently placed in patients' care areas and is relatively inexpensive. I have found in practice, however, that the cap-like cover known in the art is clumsy to apply and difficult to remove from the stethoscope head without care-providers fingers touching the patient-contact area of the cover. The latter is a problem because microbes transferred from the patient to the cover in the course of its use can be transferred to the care-provider's fingers and thence to another patient if the care-provider's fingers touch the patient-contact area of the successive cover or directly contact the patient. The full length stethoscope sleeve is advantageous in that it protects entire stethoscope from contamination from patient. However, it is relatively expensive and I have found it to be clumsy to apply and labor-intensive to use. Moreover, its typical mode of use as well as its somewhat awkward removal from a stethoscope does not easily prevent users from touching the patient-contact area. The sleeve thus still retains significant potential for microbial transmission from the patient to the cover and then to the care-provider and thence to other patients.

Another known alternative, disclosed in U.S. Pat. No. 5,747,751, is a disposable cover formed as a seamless casing with an open end wide enough to permit introduction of the stethoscope head into the casing. With this cover, too, there is a significant possibility that the user's fingers will touch the patient-contact area before and/or after examining the patent, with the attendant transfer of microbes from the user to the patient or vice versa.

The present invention is directed in one aspect to an improved disposable cover for stethoscopes or other devices. (Hereinafter reference is made solely to stethoscopes but those in the art will appreciate that the principles of the invention could be applied to disposable covers for other devices as well.) The improved cover is a "no-contact cover" in that its configuration makes it significantly easier for a user—also referred to herein as a "care-provider"—to a) place the cover on the stethoscope, b) use the stethoscope to examine a patient, and c) remove of the cover after use, all without the stethoscope head directly contacting the patient or with the user contacting the patient-contact portion of the cover either before, during or after use.

DRAWINGS

Figure 14A:
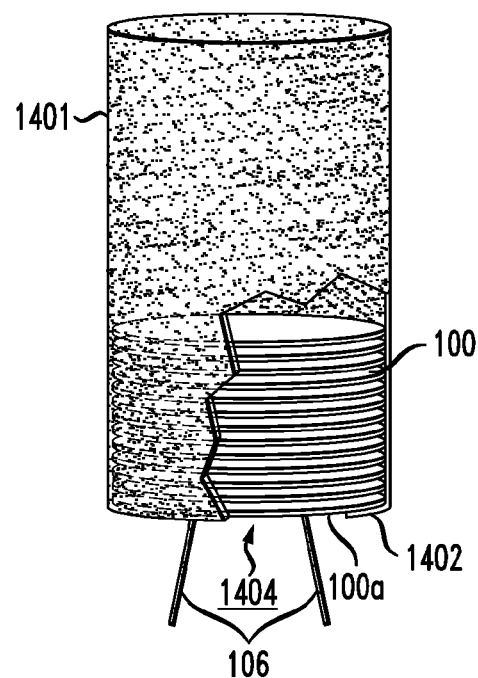
FIGS. 14A and 14B are partial cutaway front and side views, respectively, of a dispenser for covers as disclosed here wherein the covers are represented conceptually as simple disks.
Figure 14B:
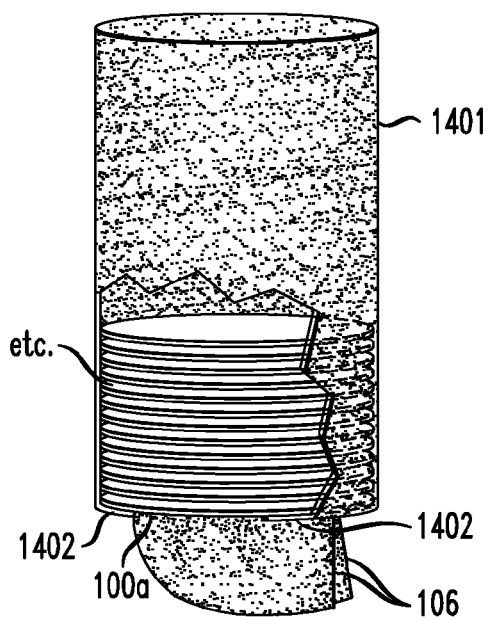
Figure 14C:
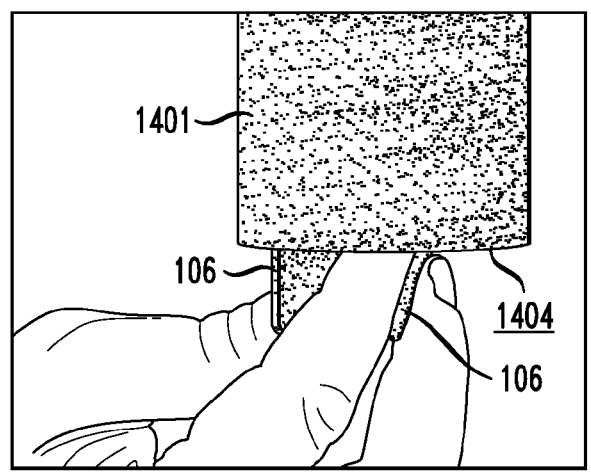
Figure 14D:
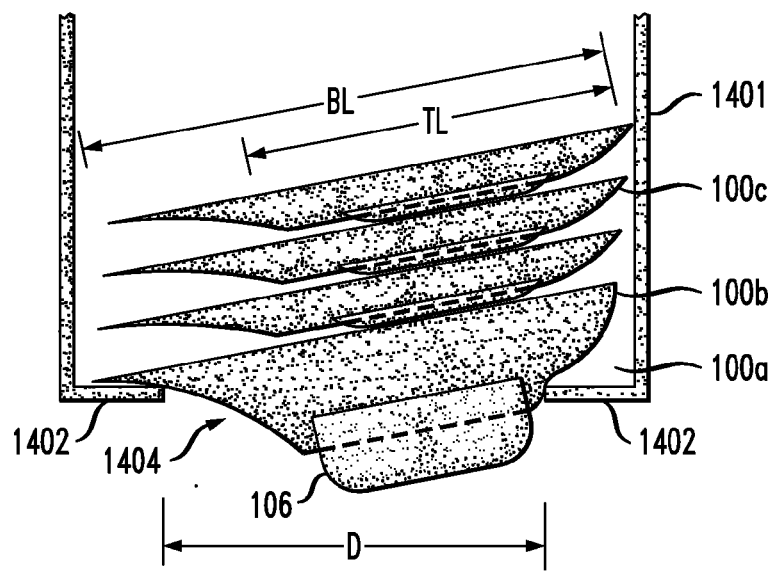
Figure 14E:
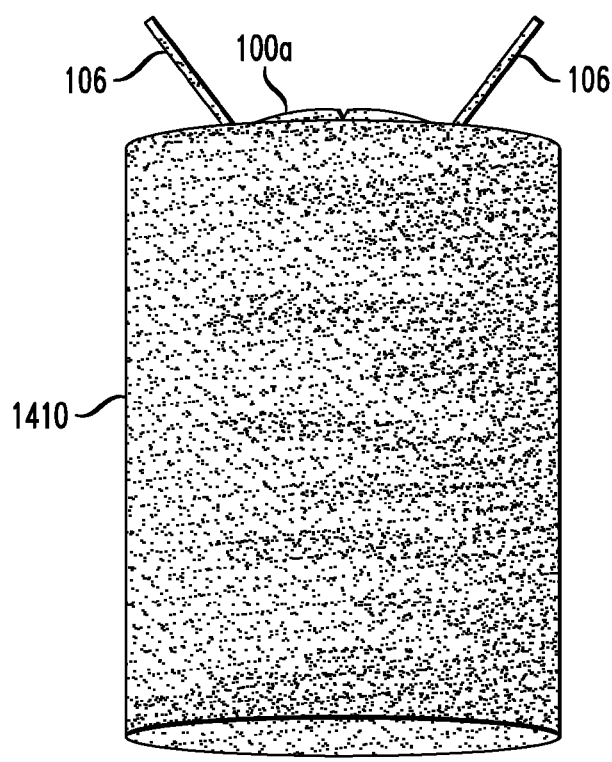

FIG. 14C shows the lower portion of the dispenser of FIGS. 14A and 14B with a care-provider's fingers being shown grasping the cover just prior to removal of same for subsequent insertion of a stethoscope head into the cover per the time sequence depicted in FIGS. 2A through 2D; and FIG. 14D is a cross-sectional view of the lower portion of the dispenser of FIGS. 14A and 14B with a more detailed presentation of the covers within the dispenser; and FIG. 14E shows an alternative form of dispenser.

DETAILED DESCRIPTION

Figure 1A:
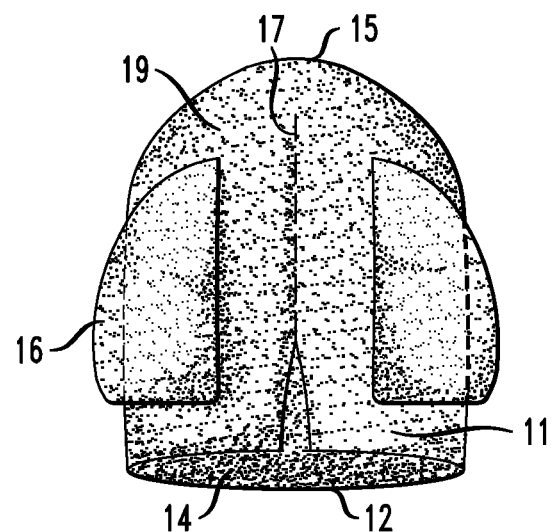
FIGS. 1A and 1B are top and side views, respectively, of a cover for a stethoscope, medical device or other article.
Figure 1B:
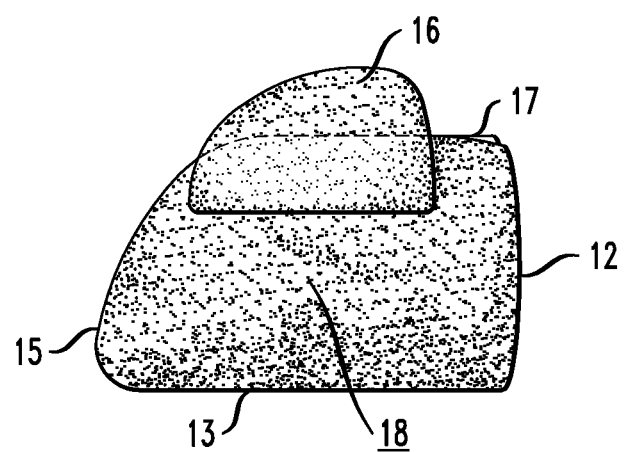

FIGS. 1A and 1B are top and side views, respectively, of a cover 10 embodying the principles of the present invention. The body of cover 10 is in the form of a bag or pouch 11 having an opening 14 at a back end thereof. The rim of the opening is indicated at 12. Pouch 11 includes a bottom, or bottom portion, 13, the outside surface of which is the patient-contacting surface. Pouch 11 also includes a top, or top portion, 19, on which are disposed a pair of rigid or at least somewhat rigid tabs 16 forward of opening 14. Tabs 16 (as well as each of the other pairs of tabs of the various embodiments disclosed herein) extend substantially in a direction between the front and back of the pouch. Between the top and bottom portions is a front portion 15 and side portions 18. Formed in top portion 19 is a perforation 17 that extends along top portion 19 from rim 12 and between tabs 16, perforation 17 being a region of structural weakness in the top of the cover.

Figure 2A:
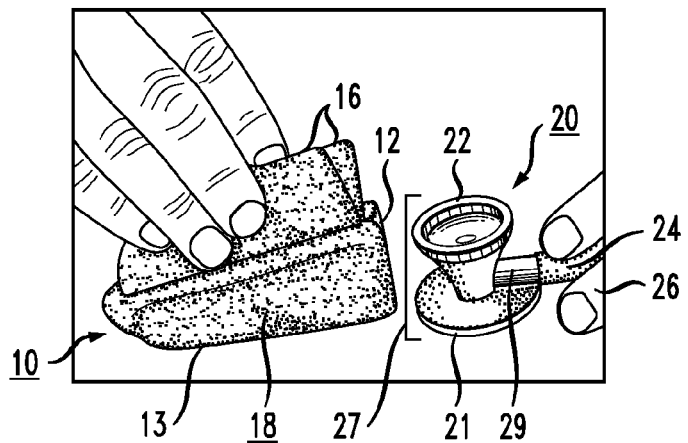
FIGS. 2A through 2D illustrate a time sequence of the insertion of a stethoscope head into the cover shown in FIGS. 1A and 1B.

FIGS. 2A through 2D illustrate a time sequence of the insertion of the head 27 of a stethoscope 20 into cover 10 of FIGS. 1A and 1B. Stethoscope head 27 includes a diaphragm 21 and a bell 22. Attached to (or regarded as part of) head 27 is conduit-connecting port 29 onto which is fitted a conduit (technically called "tubing") 24 leading to the rest of the stethoscope (e.g., an ear pipe and ear tips). In the view of FIG. 2A, a care provider or other user is holding cover 10 by grasping tabs 16 with his fingers. Illustratively the user holds one of tabs 16 between his thumb and index finger of one hand and holds the other one of tabs 16 between his index finger and his middle finger of that hand. The user is holding the stem or tubing of the stethoscope with his other hand.

Figure 2B:
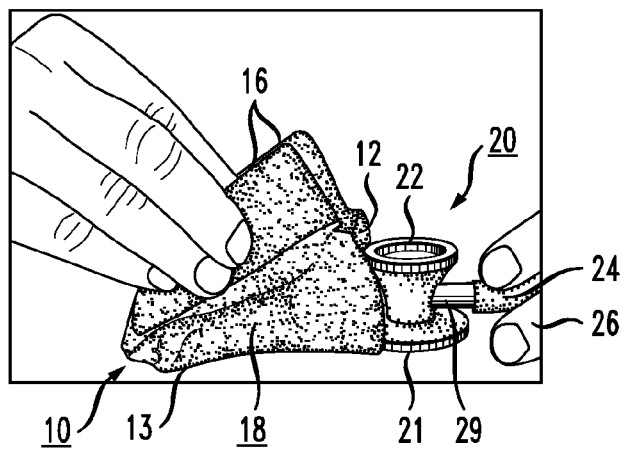
Figure 2C:
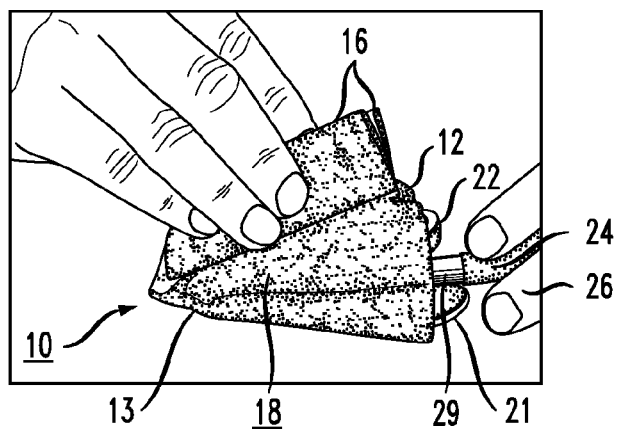
Figure 2D:
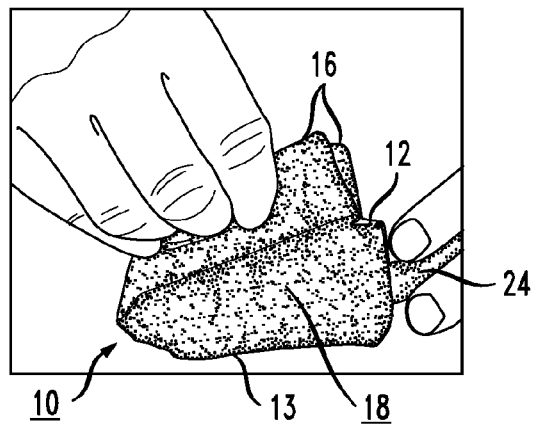

In the view of FIG. 2B, the user has partially inserted the stethoscope head 27 into pouch 11 through opening 14 by resting stethoscope head 27 on the bottom of rim 12 and pressing downward while lifting up slightly on cover 10, thereby somewhat expanding opening 14 to facilitate entry of stethoscope head 27 into pouch 11. FIG. 2C shows a further stage of insertion of the stethoscope head 27 into pouch 11 and FIG. 2D shows stethoscope head 27 fully inserted. Note that the entire stethoscope head is at this point contained within pouch 11.

Figure 2E:
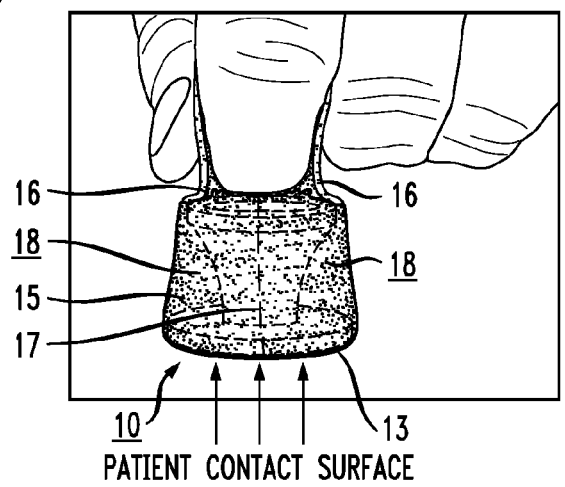
FIG. 2E is a view of the cover of FIGS. 1A and 1B as it may be held in a care-provider's hand after the stethoscope head has been inserted into the cover

At this point the user pulls or tugs on tabs 16 to pull them toward each other using his thumb and third finger lateral to the index finger as shown in FIG. 2E. Because of how tabs 16 are spaced apart from one another and of how they are disposed on the top of the pouch, the user's pulling of the tabs toward one another causes the patient contact portion of the cover, i.e. its bottom, to be pulled tight against the stethoscope diaphragm (or bell). With the cover thus held, the user can move the covered stethoscope head to whatever position is desired on the patient's body. The tabs become the mechanism by which the stethoscope head is manipulated and repositioned during the physical examination. (The bell and diaphragm usually rotate upon an axis. This could be accomplished within the cover in its loose configuration, prior to when the tabs are brought together.)

Cover 10 is illustratively made from a relatively non-stretching material, i.e., one that doesn't have much "give" when tension is applied to opposing edges of the material, an example being nonwoven cloth. This may be preferred in some embodiments because, as compared to a material that is more "stretchy," a cover made of a non-stretching material may be less likely to give rise to "bagging," ripples or other non-planarities at the interface between the cover and the patient's skin that could interfere with efficient transfer of acoustic energy (e.g., the sound of the patient's heartbeat). If a material that is more elastic, or "stretchy," is used, ripples or other non-planarities might develop at that interface depending on how the user happens to be pulling on tabs 16.

An advantage of particular covers embodying the principles of the invention, such as that shown in FIGS. 1A and 1B is that, on the one hand, a cover can be made large enough to accommodate stethoscope heads of varying sizes from small pediatric stethoscopes to large multi-head adult stethoscopes while, on the other hand, the patient-contacting surface can still be pulled taut across the diaphragm by virtue of the ability of the user to pull tabs 16 toward each other as much as necessary in order to achieve that tautness.

Note that both a) insertion or covering of the stethoscope head and b) manipulation of the covered stethoscope head are achieved without the user having to touch the patient-contacting surface of the cover, i.e. the outside surface of bottom portion 13, thereby reducing or substantially eliminating the transmission of microbes a) from the patient's skin to the stethoscope or the user's hand and b) from the stethoscope or the user's hand to the patient. In addition, the user can do what's needed without directly touching the stethoscope head.

Figure 2F:
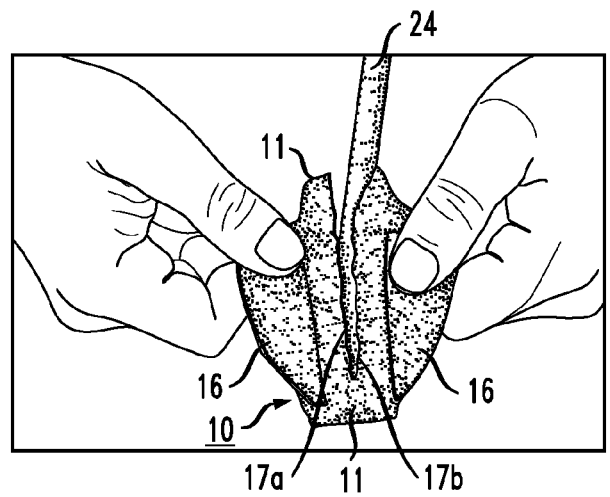
FIG. 2F illustrates how the cover may be removed from the stethoscope after use.

FIG. 2F shows that after use, cover 10 can be removed from the stethoscope by the user pulling on each of tabs 16 laterally, i.e. in respective directions away from perforation 17. This causes the left and right (as viewed from the top) sections of top portion 19 to separate along perforation 17. The two edges of those two sections that had been joined at perforation 17 are indicated in the FIGS. 17a and 17b, respectively. Note that the removal process as just described gives the user an opportunity to readily remove the cover from the stethoscope without the user having to touch the patient-contacting surface, i.e. the outside surface of bottom portion 13, thereby reducing or substantially eliminating the transmission of microbes from the cover's patient-contacting surface to the hand(s) of the user during the cover-removal process.

Removal of the cover from the stethoscope without the user having to touch the patient-contacting surface might be readily achievable without having to pull the cover apart as shown in FIG. 2F in the case of embodiments in which the opening is relatively large. In other embodiments disclosed herein, however, the opening may be elasticized or otherwise constricted, an advantage of that being that the cover captures the stethoscope head to some extent so as to reduce any likelihood of the cover becoming dislodged from the stethoscope during use. However, the constricted nature of the opening of such embodiments might make it awkward and/or very difficult for a user still holding the tabs with one hand to simply pull the stethoscope out of the cover (or, equivalently, to pull the cover off of the stethoscope) with the other hand. By providing a mechanism by which the cover is removed by being torn apart, as depicted in FIG. 2F, the possibility that the user might well touch the patient-contacting surface of the cover in the process of removing the cover from the stethoscope—with a resultant transfer to the user's fingers of microbes that transferred to the cover from the patient's skin—is significantly reduced. Indeed, in general, a snug fit of the stethoscope within the cover—and thus its removal by pulling the cover apart—are desirable so as reduce the possibility of non-planarities and so that cover will not be clumsy in use. Additionally, the looser the cover is over the stethoscope, the more likely it is that the cover will accidentally dislodge completely during use.

The same processes of stethoscope insertion, manipulation and cover removal depicted in FIGS. 2A through 2F as applied to cover 10 are equally applicable to the other covers about to be described.

Figure 3A:
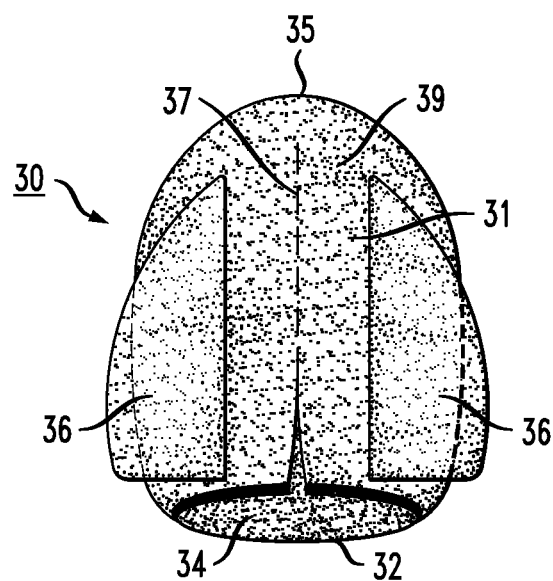
FIGS. 3A and 3B are top and side views, respectively, of another cover for a stethoscope, medical device or other article.
Figure 3B:
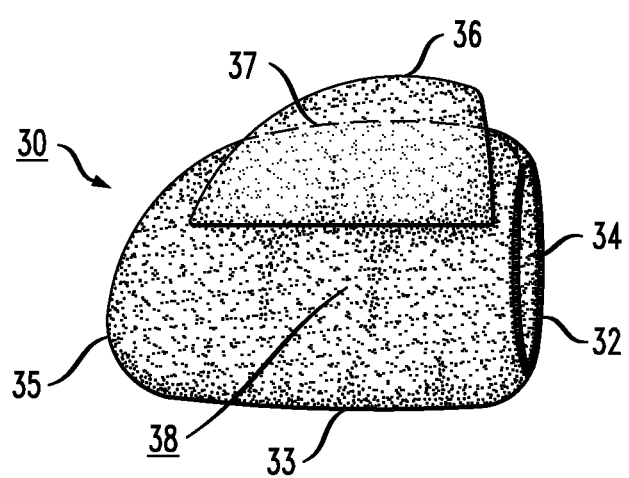

The cover of FIGS. 3A and 3B, cover 30, includes elements similar to those in the cover of FIGS. 1A and 1B. Thus the body of cover 30 is in the form of a bag or pouch 31 having an opening 34 with its rim 32; bottom portion 33; top portion 39 in which is formed perforation 37; front portion 35; side portions 38; and tabs 36 forward of opening 34.

The principal difference between the two covers 10 and 30 is that the rim 32 of opening 34 is elasticized by, for example, having an elastic cord or string affixed thereto, or embedded therein. Opening 34 is sized such that a) the force of the stethoscope head against the rim as the user pushes with one hand while the cover is held fixed by the user's other hand causes the elastic rim to expand and allow the head to pass into the inside of cover 30, after which b) the elastic cord closes back down to its original size, thereby helping to keep the cover from possibility slipping off the stethoscope head. The mechanism shown in FIG. 2F—wherein the cover is removed by pulling the tabs apart to as to cause the perforation to tear and allowing the left and right sections of the top portion of the cover to separate—is particularly advantageous in covers such as the cover of FIGS. 3A and 3B in which the rim of the opening is elasticized. Without that cover-tearing mechanism being available, so that the cover would be removed by pulling the stethoscope head out through the elasticized rim, the process of manipulating the cover and stethoscope in order to achieve this might add enough (albeit small) awkwardness to the removal process as to cause even the careful user to inadvertently touch the patient-contacting surface of the cover, whereby microbes on that surface might be transferred to the user's hand. The tabs can also be the mechanism for no-contact cover removal without needing the perforation. The perforation does, however, enhance the ability to remove the cover without contacting the patient-contaminated portion of the cover.

Figure 4A:
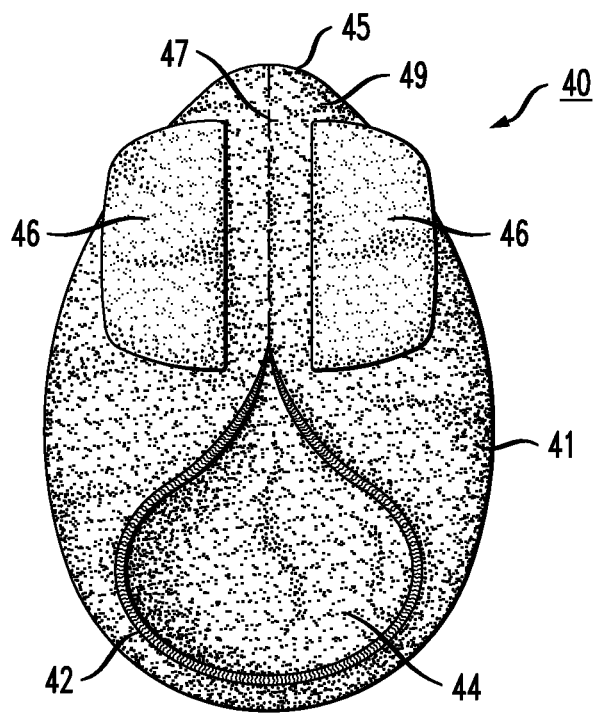
FIGS. 4A and 4B are top and side views, respectively, of another cover for a stethoscope, medical device or other article.
Figure 4B:
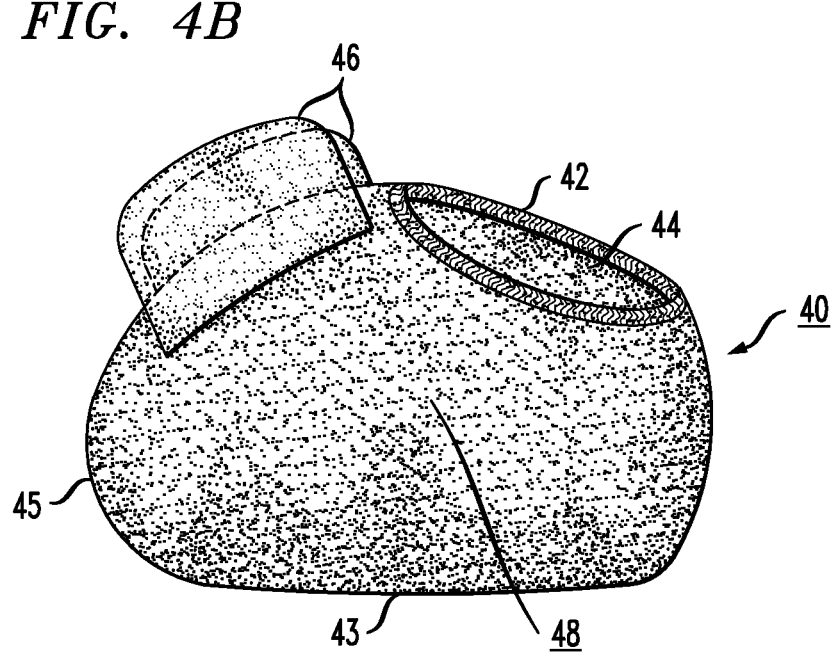

The cover of FIGS. 4A and 4B, cover 40, includes elements similar to those in the previously described covers. Thus the body of cover 40 is in the form of a bag or pouch 41 having an opening 44 with its rim 42; bottom portion 43; top portion 49 in which is formed perforation 47; front portion 45; side portions 48; and tabs 46 forward of opening 44.

In this cover, rim 42 is elasticized as in the cover of FIGS. 3A and 3B, although in other embodiments of a cover like cover 40, the rim could be non-elasticized. The principal difference between the cover of FIGS. 4A and 4B and those previously described is the location of opening 44. In the two previously described covers, openings 14 and 34 are substantially at the "back" of the cover, i.e. directly across from front portions 15 and 35, respectively. Here, opening 44 is formed in part in the back of the cover and in part on the top of the cover behind tabs 46. Certain users may find this alternative more convenient in terms of stethoscope insertion, manipulation and/or removal.

Figure 5A:
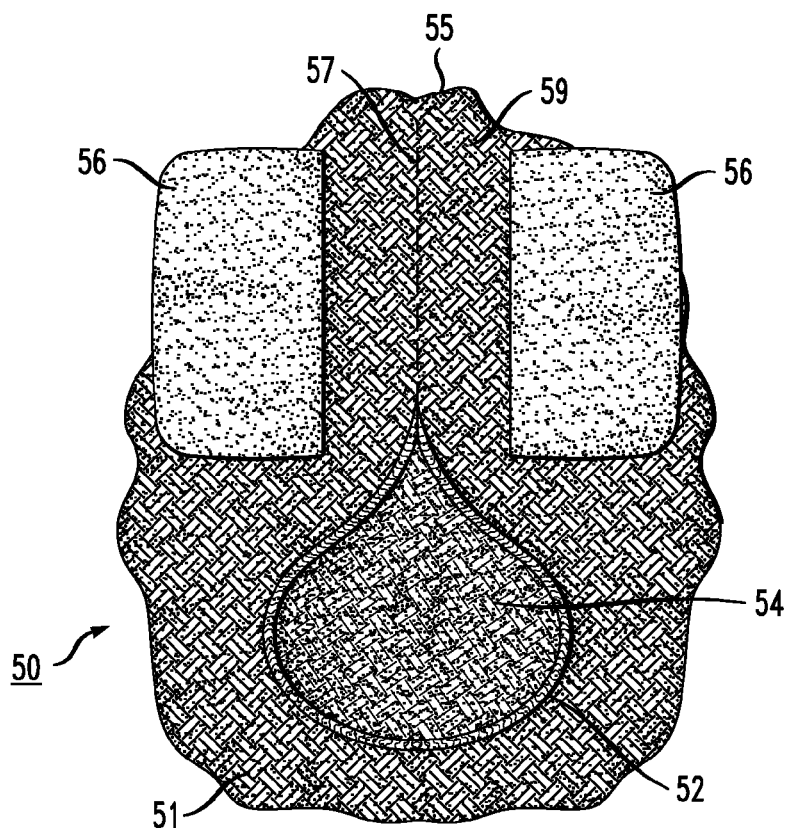
FIGS. 5A and 5B are top and side views, respectively, of another cover for a stethoscope, medical device or other article.
Figure 5B:
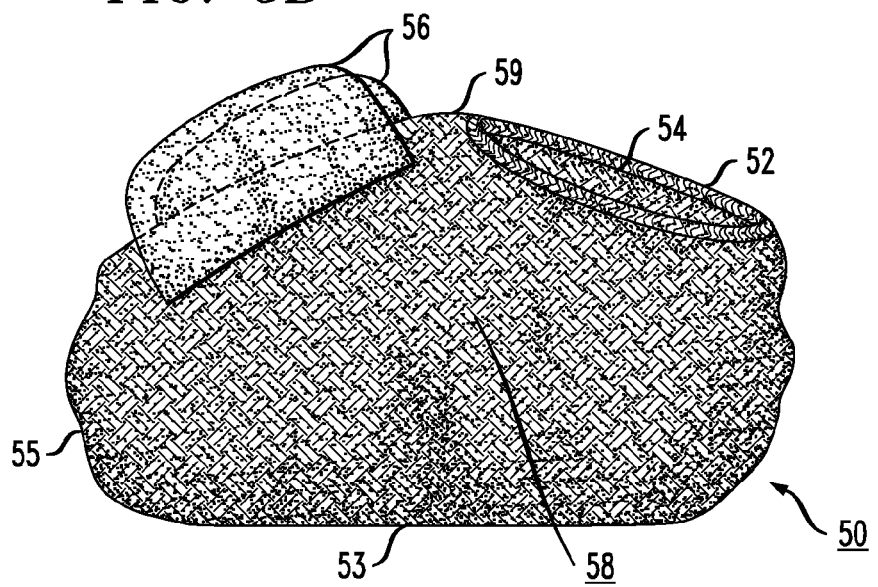

The cover of FIGS. 5A and 5B, cover 50, is similar to the cover of FIGS. 4A and 4B. Thus the body of cover 50 is in the form of a bag or pouch 51 having an opening 54 with its elasticized rim 52 (which in other embodiments could be non-elasticized); bottom portion 53; top portion 59 in which is formed perforation 57; front portion 55; side portions 58; and tabs 56 forward of opening 54. Also as in cover 40 in FIGS. 4A and 4B, opening 54 is formed in part in the back of the cover and in part on the top of the cover. In this cover, however, a more elastic, or "stretchy" material is used for the pouch. Such a material may be found more desirable than one that has little give. In order to address the possibility that a stretchy material may be more likely to give rise to non-planarities at the cover bottom, i.e., at the interface between the patient and the cover, certain covers may be made stiffer at the bottom such as by using a different material for the bottom or by introducing a stiffening agent, such as starch or wax.

Figure 6A:
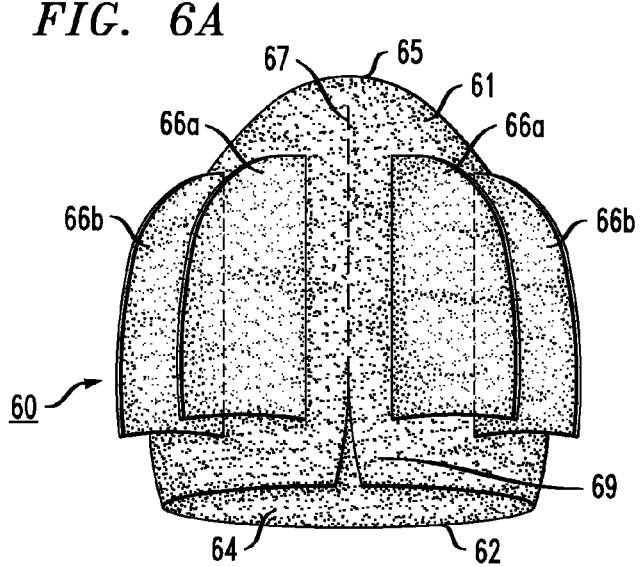
FIGS. 6A, 6B and 6C are top, side and rear views, respectively, of another cover for a stethoscope, medical device or other article.
Figure 6B:
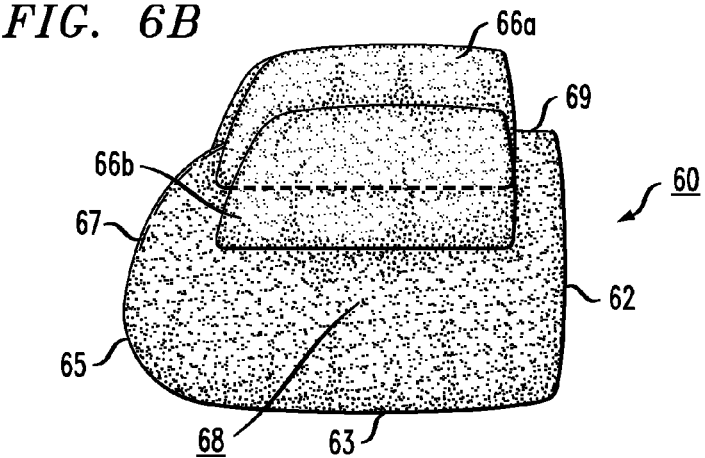
Figure 6C:
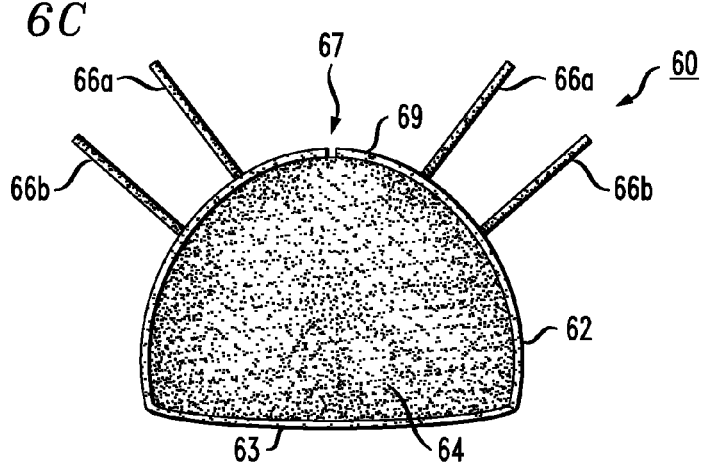

The cover of FIGS. 6A through 6C, cover 60, is similar to the cover of FIGS. 1A and 1B except that it has a second pair of tabs. Thus, the body of cover 60 is in the form of a bag or pouch 61 having an opening 64 with its rim 62; bottom portion 63; top portion 69 in which is formed perforation 67; front portion 65; side portions 68; and tabs 66a forward of opening 64. However, cover 60 has a second pair of tabs 66b that, like tabs 66a extend generally in direction between the front and back of the pouch. Each of tabs 66b is adjacent to and outboard of, a respective one of tabs 66a. Depending on such factors as the size of pouch 61 overall, the size of the stethoscope being used at a particular time, the size of the user's hands or even just user preference, the user may choose to grab onto tabs 66b, rather than tabs 66a or, perhaps, even one of each.

Figure 7A:
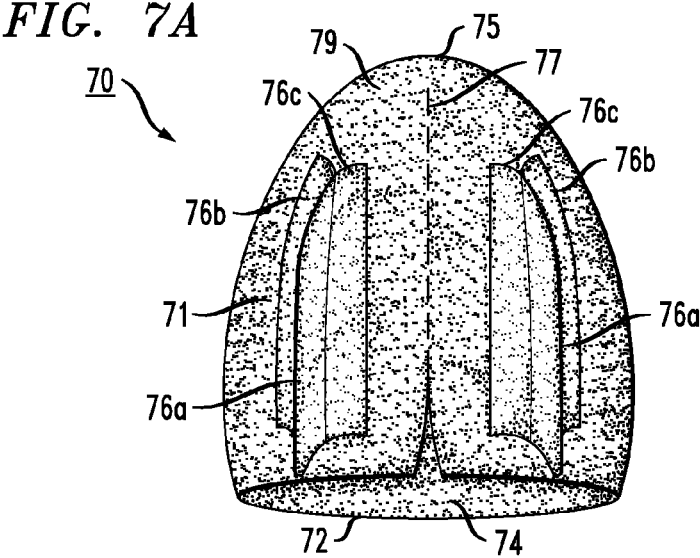
FIGS. 7A, 7B and 7C are top, side and rear views, respectively, of another cover for a stethoscope, medical device or other article.
Figure 7B:
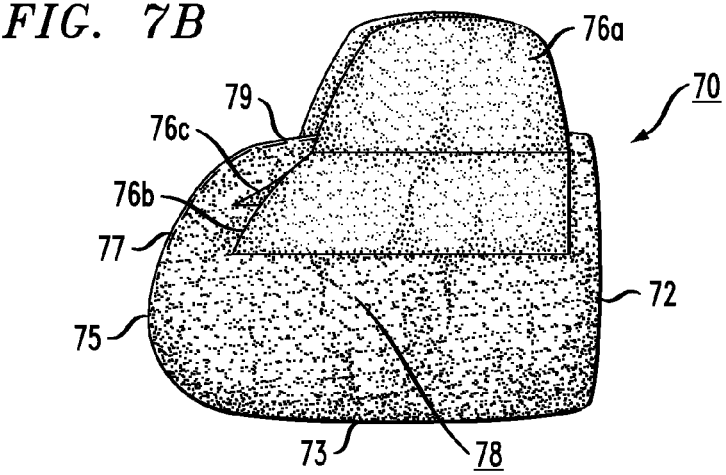
Figure 7C:
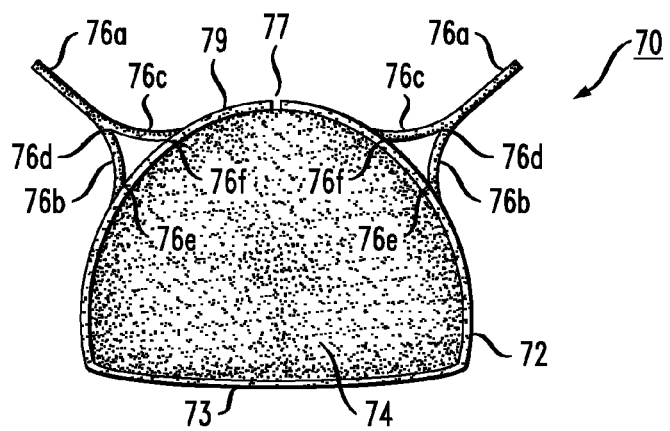

The cover of FIGS. 7A through 7C, cover 70, is similar to the cover of FIGS. 1A and 1B except as to the conformation of its tabs. Thus, the body of cover 70 is in the form of a bag or pouch 71 having an opening 74 with its rim 72; bottom portion 73; top portion 79 in which is formed perforation 77; front portion 75; and side portions 78. Also like the cover of FIGS. 1A and 1B, cover 70 has a single pair of tabs 76a forward of opening 74 that the user will grab onto. However, tabs 76a are affixed or otherwise formed to be integral with pouch 71 by scaffolding comprising scaffold parts 76b and 76c arranged in a generally V-shaped, or tent-shaped, configuration wherein the bottoms of tabs 76a are connected to the ridge 76d (shown in FIG. 7C) of the tent shape and wherein the bottoms 76e and 76f of the scaffold parts 76b and 76c are affixed or otherwise formed to be integral with top portion 79 of pouch 71. Like the cover of FIGS. 6A through 6C, this cover may allow the bottom of the cover to be pulled taut against the stethoscope diaphragm while still accommodating variations in such factors as the size of the pouch overall, the size of the stethoscope being used at a particular time or the size of the user's hands. An advantage of the scaffolding is that the scaffold parts 76b provide extra leverage in order to close the cover tightly around smaller stethoscope heads and the scaffold parts 76*c* provide the leverage that makes it easier to tear the perforation. Another advantage of having the scaffolding is that it may allow a cover to accommodate a greater range of stethoscope head sizes than non-scaffolded versions. A reason is that non-scaffolded versions, when large enough to accommodate the bulkiest of stethoscope heads, may be too loose or floppy when used for pediatric/small heads even when the non-scaffolded tabs are pulled together. By the same token, the opening of a cover small enough to work well with smaller stethoscope heads may provide be too small for larger stethoscope heads to be introduced. Those skilled in the art will be readily able to determine appropriate dimensions of the tabs and scaffolding parts, including the distance between bottoms 76*e* and 76*f* of the scaffold parts 76*b* and 76*c*, in order to achieve these advantages.

Figure 8A:
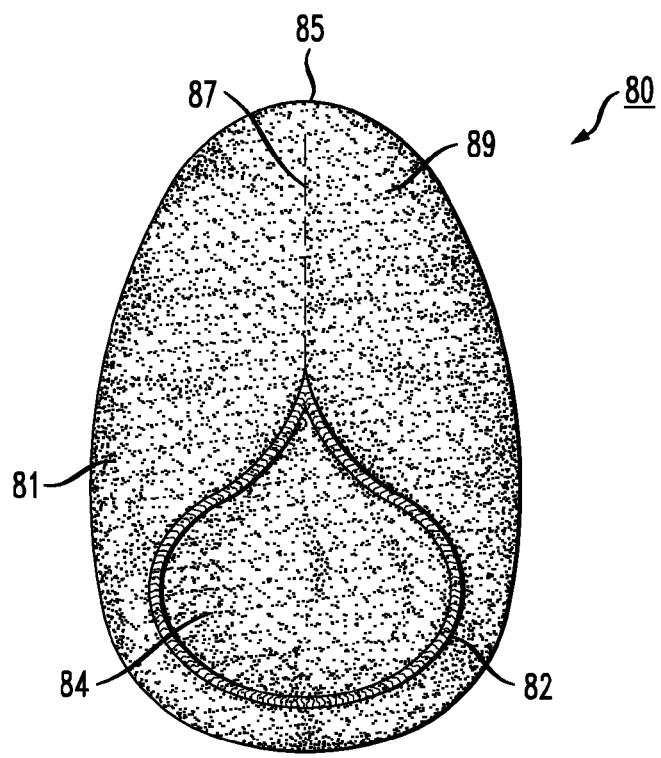
FIGS. 8A and 8B are top and side views, respectively, of another cover for a stethoscope, medical device or other article.
Figure 8B:
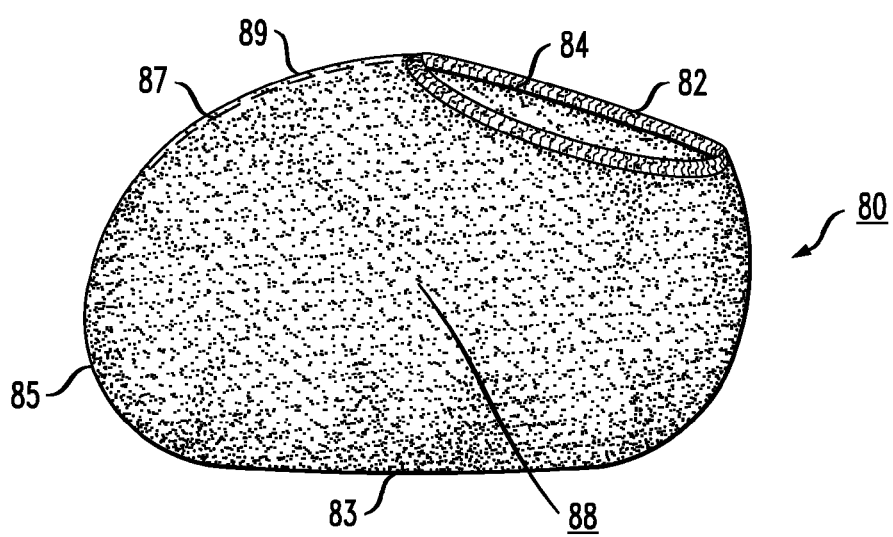
Figure 9A:
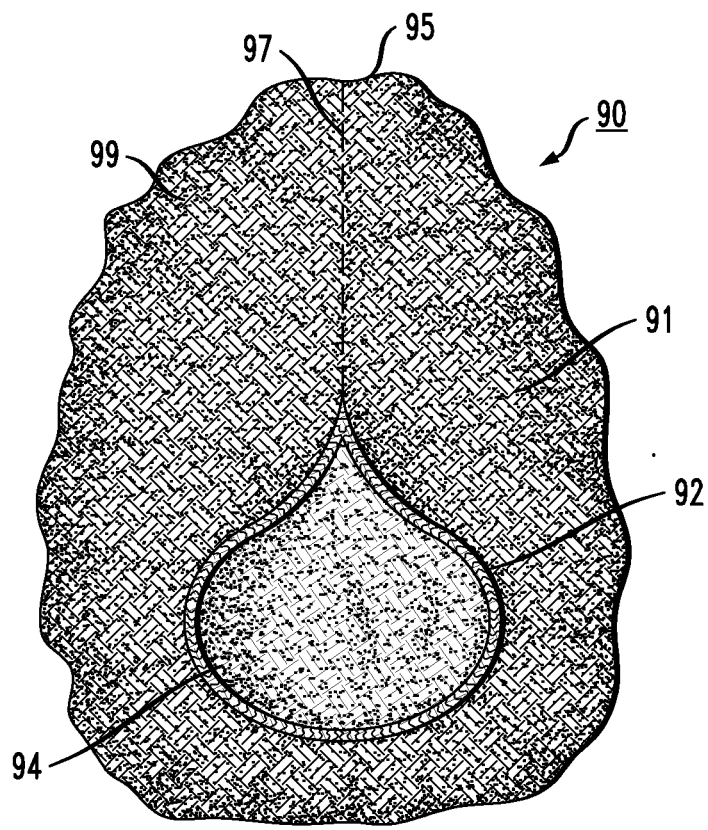
FIGS. 9A and 9B are top and side views, respectively, of another cover for a stethoscope, medical device or other article.
Figure 9B:
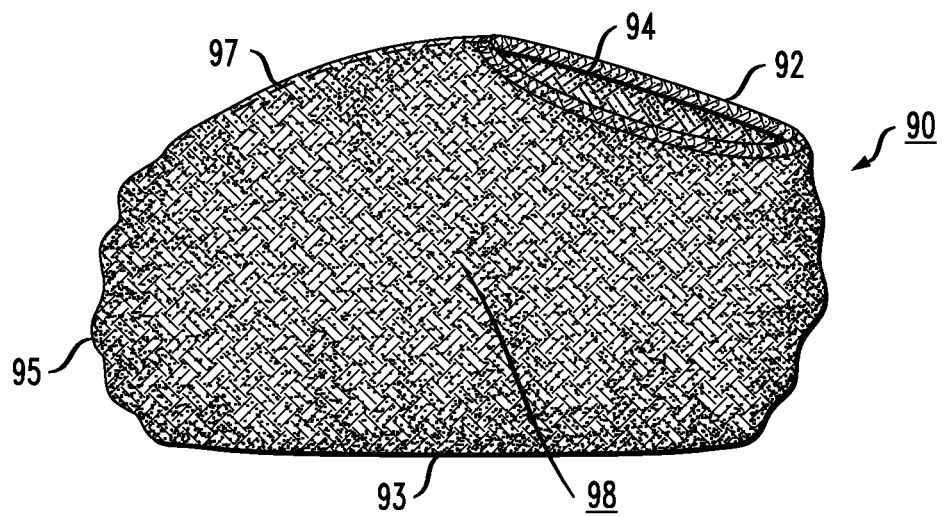

FIGS. 8A and 8B depict a cover 80 that is similar to cover 50 shown in FIGS. 5A and 5B except that cover 80 does not have any tabs and it is made of a relatively non-stretchy material. Thus the body of cover 80 is in the form of a bag or pouch 81 having an opening 84 with its elasticized rim 82 (which in other embodiments could be non-elasticized); bottom portion 83; top portion 89 in which is formed perforation 87; front portion 85; and side portions 88. The lack of tabs in cover 80 means that some of the advantages of having the tabs may not be present. In particular, cover 80 does not afford the user with the same degree of convenience and/or leverage that is provided by the previously described covers in terms of, for example, being able to pull the bottom of the cover taut against the stethoscope diaphragm. Other potential disadvantages of not having tabs will be appreciated from the discussion below in connection with FIGS. 14A through 14D which illustrates how the presence of tabs facilitates easy dispensing of the covers from a dispenser while reducing the possibility that a user's hand(s) will touch the patient-contacting surface of the cover. On the other hand, cover 80 is simpler and, it is believed, less expensive to manufacture. Additionally, cover 80 can nonetheless be sized so as to be able to accommodate various stethoscope sizes and to allow the user to pinch or gather the sides of top portion 89 together between the user's thumb, on the one side and one or more fingers on the other side and thereby pull the bottom of the cover taut against the diaphragm. Moreover, advantageously, cover 80 can still be removed after use in a way that reduces the likelihood of post-use contact between the patient-contacting surface and the user's hand(s). Specifically, the user can grab the left and right portions of top portion 89 and pull the cover apart—and thus off of the stethoscope head—in a manner similar to the way it could be done as shown in FIG. 2F for covers that do have tabs. FIGS. 9A and 9B depict a cover 90 that is similar to cover 80 shown in FIGS. 8A and 8B. Thus the body of cover 90 is in the form of a bag or pouch 91 having an opening 94 with its elasticized rim 92 (which in other embodiments could be non-elasticized); bottom portion 93; top portion 99 in which is formed perforation 97; front portion 95 and side portions 98. The principal difference between covers 80 and 90 is that this cover is made of a stretchy material used as in cover 50, per FIGS. 5A and 5B.

Figure 10A:
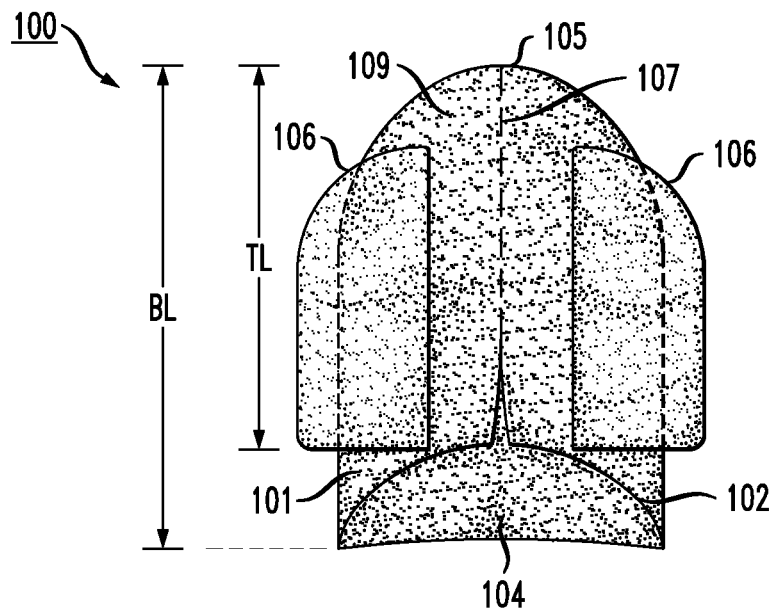
FIGS. 10A and 10B are top and side views, respectively, of another cover for a stethoscope, medical device or other article.
Figure 10B:
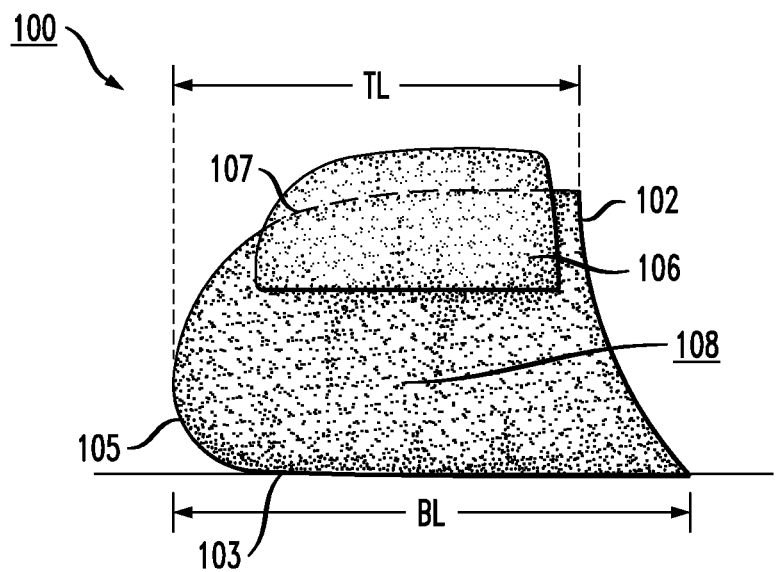

The cover of FIGS. 10A and 10B, cover 100, includes elements similar to those in the cover of FIGS. 1A and 1B. Thus the body of cover 100 is in the form of a bag or pouch 101 having an opening 104 with a rim 102; bottom portion 103; top portion 109 in which is formed perforation 107; front portion 105 and tabs 106 forward of opening 104.

The principal difference between covers 10 and 100 is that in cover 100, the length of the top of the cover—the dimension TL—is shorter than the length of the bottom of the cover—the dimension BL, as a result of which the rim 102, rather than being generally circular like rim 12 of cover 10, is somewhat elliptical. Others of the embodiments disclosed herein may be modified to be dimensioned in this way. Such dimensioning of a cover may be advantageous in enabling it to be dispensed from a dispenser from an initial folded-flat configuration to a ready-to-use configuration in which the cover's opening is ajar and ready to receive a stethoscope, as shown, for example, in FIG. 2A. This is discussed more fully herein below in conjunction with the description of FIGS. 14A through 14D.

Figure 11A:
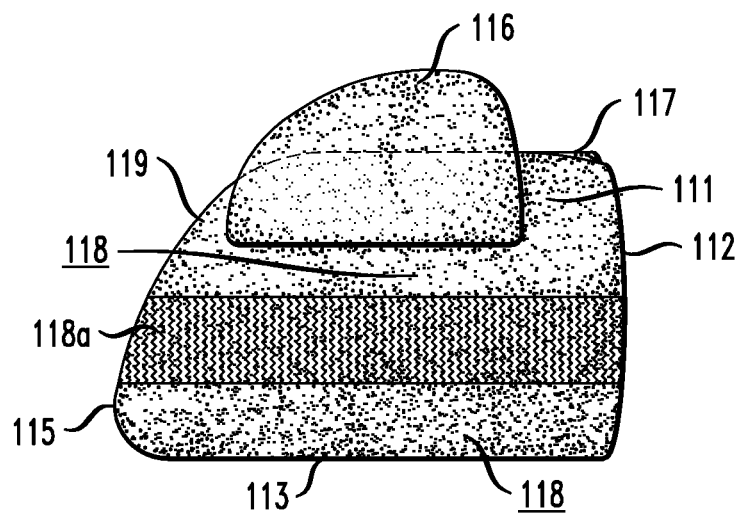
FIGS. 11A and 11B are side and rear views, respectively, of another cover for a stethoscope, medical device or other article.
Figure 11B:
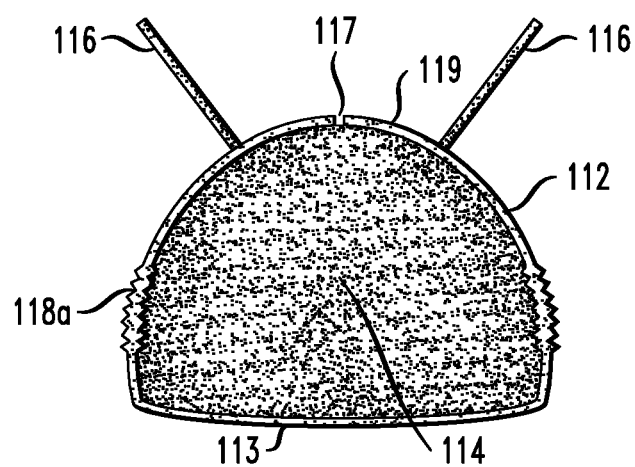

The cover of FIGS. 11A and 11B, cover 110, includes elements similar to those in the cover of FIGS. 1A and 1B. Thus the body of cover 110 is in the form of a bag or pouch 111 having an opening 114 with its rim 112; bottom portion 113; top portion 119 in which is formed perforation 117; front portion 115; side portions 118 and tabs 116 forward of opening 114.

The principal difference between the two covers 10 and 110 is that side portions 118 include an elastic side panel, or band, 118*a*, which allows for the accommodation of a wider range of stethoscope head sizes than would otherwise be the case because it allows the cover to be sized in such a way that there will be a snug fit for smaller stethoscope heads while allowing the cover to accommodate larger stethoscope heads by virtue of the fact that the elastic side panels can expand which, in essence, causes the surface area of the sides 118 to increase. In such embodiments, the tabs might be further apart from one another than in other embodiments.

Figure 12A:
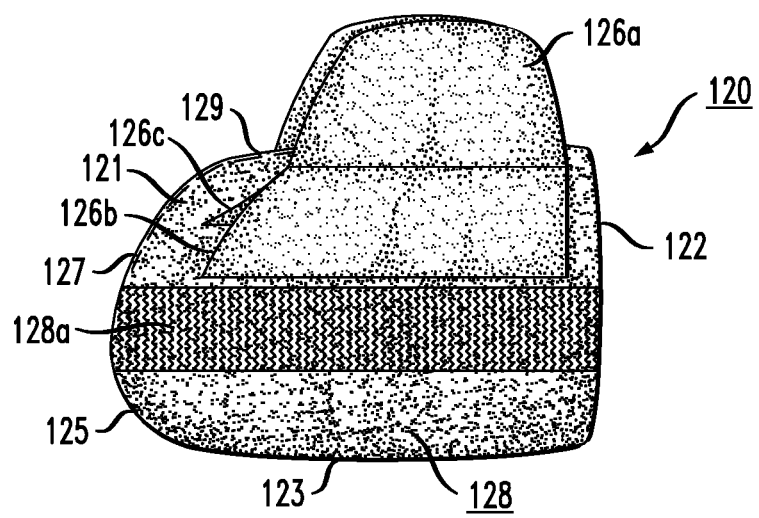
FIGS. 12A and 12B are side and rear views, respectively, of another cover for a stethoscope, medical device or other article.
Figure 12B:
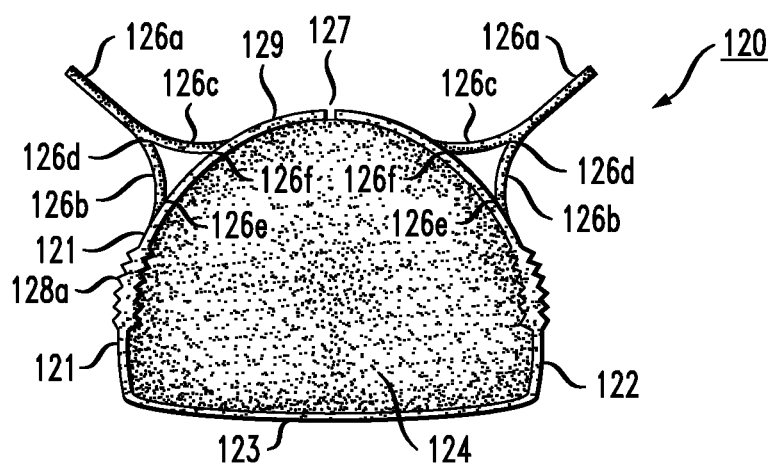

The cover of FIGS. 12A and 12B, cover 120, includes elements similar to those in the cover of FIGS. 7A and 7B. Thus the body of cover 120 is in the form of a bag or pouch 121 having an opening 124 with its rim 122; bottom portion 123; top portion 129 in which is formed perforation 127; front portion 125; side portions 128 and tabs 126*a* forward of opening 124 affixed or otherwise formed to be integral with pouch 121 by scaffolding comprising scaffold parts 126*b* and 126*c*.

The principal difference between the two covers 70 and 120 is that side portions 128 include an elastic side panel, or band, 128*a* similar to elastic side panel, or band, 118*a* of cover 110.

Figure 13A:
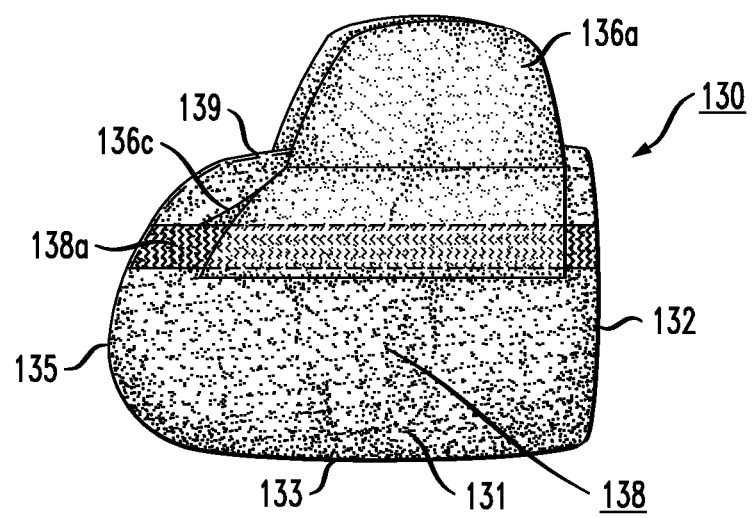
FIGS. 13A and 13B are side and rear views, respectively, of another cover for a stethoscope, medical device or other article.
Figure 13B:
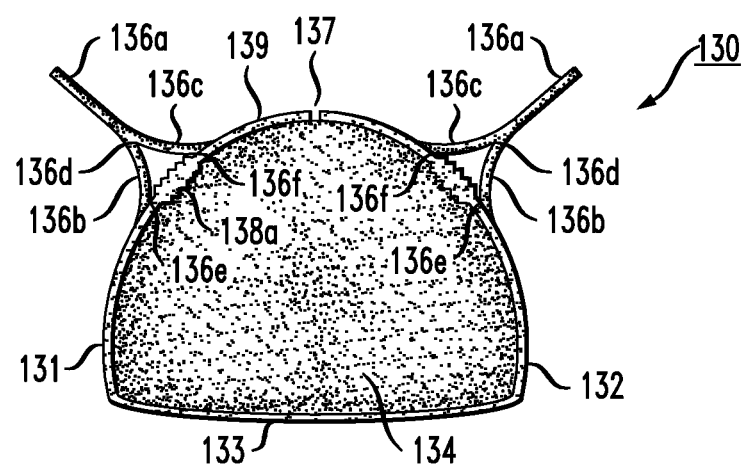

The cover of FIGS. 13A and 13B, cover 130, includes elements similar to those in the cover of FIGS. 12A and 12B. Thus the body of cover 130 is in the form of a bag or pouch 131 having an opening 134 with its rim 132; bottom portion 133; top portion 139 in which is formed perforation 137 front portion 135; side portions 138; tabs 136*a* forward of opening 134 affixed or otherwise formed to be integral with pouch 131 by scaffolding comprising scaffold parts 136*b* and 136*c*; and an elastic side panel, or band, 138*a*.

The principal difference between the two covers 120 and 130 is that elastic side panel, or band, 138*a* of cover 130 extends between scaffold parts 136*b* and 136*c* rather than further down along the side of the pouch as is the case for cover 120.

FIGS. 14A through 14E show an illustrative approach for dispensing covers having tabs as disclosed herein. Specifically, FIGS. 14A and 14B are partial cutaway front and side views, respectively, of a cylindrical dispenser 1401 having a circular cross-section in which are stacked a plurality of covers 100*a*, 100*b*, 100*c* . . . . These covers are illustratively like cover 100, shown in FIGS. 10A and 10B although represented conceptually in FIGS. 10A and 10B as simple disks. The downward-facing mouth, or orifice, 1404 of the dispenser having a rim 1402 holds the covers folded flat in a stack one on top of the other. The cover 100a at the bottom of the stack has tabs 106 protruding below the orifice of the dispenser. A user can grab the tabs in the manner shown in FIG. 14C and thereby pull that one cover from the dispenser. The user has thus been able to grab a cover with one hand without touching its patient-contacting surface.

Covers 100a, 100b, 100c—represented for simplicity as simple flat discs in FIGS. 14A and 14B—are shown in more detail in FIG. 14D. In particular, the length TL of the top of the covers is less than the diameter D of orifice 1404, whereas the length BL of the bottom of the covers is greater than D. As a result, as the bottom-most cover 100a is pulled out of the dispenser, the extra drag that is placed on its bottom portion by the protruding edge of orifice 1402 as the cover is pulled through the orifice expands the opening 104 from its closed, folded position to an open, or ajar, position, such as shown in FIG. 2A. Indeed, FIG. 14D shows cover 101a at a time when it is just beginning to be pulled out of the dispenser and is already partially expanded. As such, the cover is ready to receive a stethoscope head without the user having to have touched the bottom—or indeed any part—of the cover with his free hand.

As a cover is pulled from the container, the tabs of the cover above it—theretofore folded flat against the pouch portion of the cover—are pulled downward so as to protrude from the bottom of the dispenser. This may be achieved in any of various ways as can be devised by those skilled in the art, such as by a particular interfolding of one cover with the ones above and below it in the stack, or by attaching the tabs of each cover to the cover below it in the stack with a light-duty adhesive. Those skilled in the art may well be able to devise other ways of achieving this functionality that may be different for different covers. Another possibility is that the covers could be configured in such a way that a cover becomes ajar within the dispenser itself rather than upon being pulled therefrom.

FIG. 14E shows an alternative form of dispenser 1410, by which the covers are dispensed from the top rather than the bottom. When a cover is removed from this dispenser, another cover "pops up" similar to the way some facial tissues and wet wipes "pop up" from their containers. In order to achieve this pop-up function, it is envisioned that inside the dispenser will be a spring-biased pusher plate of some type that would push up on the stack of covers inside the dispenser, similar to the functionality of some napkin dispensers, such as that shown in U.S. Pat. No. 2,831,602. Achieving the pop-up function may also be aided by, as suggested above, the covers themselves being somewhat attached to one another via, for example, a light duty adhesive or via a particular manner of interfolding the covers one with the other.

A cover embodying the principles of the invention may be made from any generally pliable material suitable for the described functionality, including, for example, a non-woven cloth, latex, synthetic latex, paper, cotton, polyisoprene and nitrile or some combination of these or other materials. Other embodiments, particularly for other medical devices such as covers for ultra-sound probes, may benefit by using a water-proof material).

A cover embodying the principles of the invention may be manufactured in any of various ways as will be apparent to those skilled in the art. One possible way would be to begin with a single tube made out of the selected material that is then cut into "sub-tubes" to an appropriate lengthwise dimension. Each such "sub-tube" will ultimately become a cover. The front of a sub-tube is trimmed to be rounded/curved and adhesive applied to close the anterior (front) portion. In those embodiments having tabs, the tabs are then attached to the pouch using an adhesive. The tabs are cut from an additional material and made stiff using wax or other suitable substrate. For embodiments having scaffolding tabs, those tabs are produced for each side from one piece of material per side and folded over to produce the scaffolding tab. In those embodiments where the rim of the opening is elasticized, the elastic can be applied at some appropriate point in the process that may be, for example, prior to applying the tabs (if any). The perforation is also created at some appropriate point in the process, that could be, for example, just before or just after the tabs (if any) are applied. The cover as a whole is made sterile at an appropriate point during manufacture.

The physical dimensions of covers and/or of the various parts thereof embodying the principles of the invention may vary as may prove convenient for users. The following dimensions are illustrative for stethoscopes

| | |
|---|---|
| Overall length | 7-10 cm |
| Compressed width (when the cover is flat within the dispenser) | 7-9 cm |
| Compressed height | 2-4 mm |
| Height when open (not including tabs). | 5-6 cm |
| Height of tabs | 2-3.5 cm |
| Opening diameter | 5-6 cm |
| Length of perforation | 5-9 cm |

Covers for other devices may have other dimensions as will be appropriate for those devices. It is envisioned that perhaps covers embodying the principles of the invention might be used for ultrasound probes, including vaginal wands. Another possible use is for shoe covers.

The foregoing merely Illustrates the principles of the invention. For example, even though not shown or described herein, other covers may incorporate other different combinations of such features such as placement of the opening, elasticization or non-elasticization of the opening's rim, numbers of tabs (including a single tab), shapes of the tabs, stiffened versus non-stiffed bottoms of the cover, etc. Alternative arrangements for dispensing the covers are also possible, including dispensers whose cross-sections are other than circular.

Another alternative is that the tabs may be formed not as elements separate from one another but as a unitary tab subassembly having a joining member tying together the bottoms of the tabs, with the joining member then being affixed to the top portion of the pouch and with the perforation also extending through that joining member. Such a tab subassembly might be formed, for example, from a single piece of material that is bent into a U-shape wherein the base of the U is the joining member and the legs of the U are the tabs.

In the disclosed embodiments, the tabs are forward of the opening. Other embodiments—particularly embodiments in which the opening is in part at the back and in part at the top of the cover—may have the tabs behind the opening.

Covers embodying the principles of the invention can accommodate various styles of stethoscope. For example, although the stethoscope depicted herein has a bell, covers embodying the principles of the invention can accommodate stethoscopes that do not have a bell.

Covers embodying the principles of the invention might be sold as a stack to be inserted into a permanent dispenser, as depicted herein. Alternatively, the covers might be sold in a dispenser that is intended to be discarded after the covers therein have all been used.

It will thus be appreciated that those skilled in the art will be able to devise numerous arrangements which, although not explicitly shown or described herein, embody the principles of the present invention and are thus within its spirit and scope.

The invention claimed is:

1. A cover for a stethoscope, the cover comprising
a pouch having front, back, top, bottom and sides, there being formed in the pouch an opening for receiving at least a portion of the stethoscope, the opening being formed, at least in part, in the back of the pouch, the pouch being configured in such a way that the opening is opposite the front of the pouch and in such a way that a head of the stethoscope can be inserted into the pouch through the opening in a direction away from the back of the pouch and toward the front of the pouch, and
one or more tabs disposed on the top of the pouch.

2. The cover of claim 1 wherein the opening is further formed at least in part in the top of the pouch.

3. The cover of claim 1 wherein the pouch is further configured in such a way that when the head of the stethoscope is inserted into the pouch in a direction away from the back of the pouch and as far as possible toward the front of the pouch, the head of the stethoscope is prevented from further movement in that direction.

4. The cover of claim 1
wherein the cover is for a stethoscope having a head, a pair of ear tips, and at least one interconnection part interconnecting the head and the pair of ear tips,
and wherein the one or more tabs is a pair of tabs that are spaced apart from one another and that are disposed on the top of the pouch in such a way that a user can cause the bottom of the pouch to be pulled taut against the head of the stethoscope when a) the head of the stethoscope is within the pouch and the ear tips and at least a portion of the at least one interconnection part are outside of the pouch, and b) the user holds each of the tabs between a respective pair of digits of a hand of the user, and c) the user pulls the pair of tabs toward one another using those digits of the user's hand.

5. The cover of claim 1 wherein at least one of the tabs has at least one planar surface.

6. The cover of claim 1 wherein at least one of the tabs is made of a stiffened material.

7. The cover of claim 1 wherein said opening is the only opening formed in said pouch.

8. A cover for a stethoscope, the cover comprising
a pouch having front, back, top, bottom and sides, there being formed in the pouch an opening for receiving at least a portion of the stethoscope, the opening being formed, at least in part, in the back of the pouch, and
one or more tabs disposed on the top of the pouch,
wherein the one or more tabs comprise at least a first pair of tabs, each of the tabs of the first pair of tabs extending substantially in a direction from the front of the pouch to the back of the pouch.

9. The cover of claim 8 wherein the opening is further formed at least in part in the top of the pouch.

10. The cover of claim 8
wherein the cover is for a stethoscope having a head, a pair of ear tips, and at least one interconnection part interconnecting the head and the pair of ear tips,
and wherein the one or more tabs is a pair of tabs that are spaced apart from one another and that are disposed on the top of the pouch in such a way that a user can cause the bottom of the pouch to be pulled taut against the head of the stethoscope when a) the head of the stethoscope is within the pouch and the ear tips and at least a portion of the at least one interconnection part are outside of the pouch, and b) the user holds each of the tabs between a respective pair of digits of a hand of the user, and c) the user pulls the pair of tabs toward one another using those digits of the user's hand.

11. The cover of claim 8 wherein at least one of the tabs has at least one planar surface.

12. The cover of claim 8 wherein at least one of the tabs is made of a stiffened material.

13. The cover of claim 8 wherein said opening is the only opening formed in said pouch.

14. A cover for a stethoscope of a type having a head, a pair of ear tips, and at least one interconnection part interconnecting the head and the pair of ear tips, the cover comprising
a pouch having front, back, top, bottom and sides, there being formed in the pouch an opening for receiving the head of the stethoscope, the opening being formed, at least in part, in the back of the pouch, and
one or more tabs disposed on the top of the pouch,
wherein the one or more tabs comprise a pair of tabs that are spaced apart from one another and are disposed on the top of the pouch in such a way that when the pair of tabs are pulled toward one another with the head of the stethoscope being as far within the pouch as possible, the bottom of the pouch is caused to be pulled taut against the head of the stethoscope.

15. The cover of claim 14 wherein the opening is further formed at least in part in the top of the pouch.

16. The cover of claim 14 wherein at least one of the tabs has at least one planar surface.

17. The cover of claim 14 wherein at least one of the tabs is made of a stiffened material.

18. The cover of claim 14 wherein said opening is the only opening formed in said pouch.

19. A cover for a stethoscope, the cover comprising
a pouch having front, back, top, bottom and sides, there being formed in the pouch an opening for receiving at least a portion of the stethoscope, the opening being formed, at least in part, in the back of the pouch, and
one or more tabs disposed on the top of the pouch,
wherein the one or more tabs comprises a first tab having a linear bottom attached to said top along a line and a second tab having a linear bottom attached to said top along a line,
and wherein the lines along which the first and second tabs are attached to the top each extend substantially in a direction from the front of the pouch to the back of the pouch.

20. The cover of claim 19 wherein the opening is further formed at least in part in the top of the pouch.

21. The cover of claim 19
wherein the cover is for a stethoscope having a head, a pair of ear tips, and at least one interconnection part interconnecting the head and the pair of ear tips,
and wherein the first and second tabs are spaced apart from one another and are disposed on the top of the pouch in such a way that a user can cause the bottom of the pouch to be pulled taut against the head of the stethoscope when a) the head of the stethoscope is within the pouch and the ear tips and at least a portion of the at least one interconnection part are outside of the pouch, and b) the user holds each of the tabs between a pair of digits of a hand of the user, and d) the user pulls the pair of tabs toward one another using those digits.

22. The cover of claim 19 wherein at least one of the first and second tabs has at least one planar surface.

23. The cover of claim 19 wherein at least one of the first and second tabs is made of a stiffened material.

24. The cover of claim 19 wherein said opening is the only opening formed in said pouch.

* * * * *